(12) United States Patent
Xie

(10) Patent No.: US 6,294,717 B1
(45) Date of Patent: Sep. 25, 2001

(54) INBRED RICE LINES A0044 AND B0044

(75) Inventor: Fang Ming Xie, Pear Land, TX (US)

(73) Assignee: Ricetec, AG, Vaduz (LI)

( * ) Notice: Subject to any disclaimer, the term of this patent is extended or adjusted under 35 U.S.C. 154(b) by 0 days.

(21) Appl. No.: 09/418,888

(22) Filed: Oct. 15, 1999

(51) Int. Cl.$^7$ ............................... A01H 5/00; A01H 5/10; A01H 1/00; C12N 5/04
(52) U.S. Cl. .................. 800/320.2; 800/260; 800/271; 800/274; 435/430
(58) Field of Search ............................ 800/320.2, 298, 800/260, 267, 271, 274; 435/410, 430

(56) References Cited

U.S. PATENT DOCUMENTS

| | | |
|---|---|---|
| 4,827,664 | 5/1989 | Yuan . |
| 5,260,503 | 11/1993 | Dorman et al. . |
| 5,304,718 | 4/1994 | Ward et al. . |
| 5,304,725 | 4/1994 | Nelson . |
| 5,436,387 | 7/1995 | Arthur . |
| 5,436,390 | 7/1995 | Oestreich . |
| 5,569,814 | 10/1996 | Eby . |
| 5,574,207 | 11/1996 | Rasmussen . |
| 5,689,914 | 11/1997 | Greaves et al. . |
| 5,763,741 | 6/1998 | Payne . |
| 5,763,742 | 6/1998 | Morrison et al. . |
| 5,763,748 | 6/1998 | Sijmons et al. . |
| 5,763,749 | 6/1998 | Eby et al. . |
| 5,773,680 | 6/1998 | Foster . |
| 5,792,929 | 8/1998 | Mariani et al. . |

OTHER PUBLICATIONS

Xu. International Rice Research Notes. vol. 24, No. 3, pp. 10–11, 1999.*

X. Chen, S. Temnykh, Y. Xu, Y.G. Cho, S.R. McCouch. Development of a Microsatellite Framework Map Providing Genome–Wide Coverage in Rice (*Oryza sativa* L.) Theor Appl Genet (1997) 95:553–567.

Johnson O. Olufowote, Yunbi Xu, Xiuli Chen, William D. Park, Henry M. Beachell, Robert H. Dilday, Mak Goto and Susan R. McCouch. Comparative Evaluation of Within–Cultivar Variation of Rice (*Oryza sativa* L.) Using Microsatellite and RFLP Markers. Genome, 40:370–378 (1997).

O. Panaud, X. Chen and S.R. McCouch. Development of Microsatellite Markers Characterization of Simple Sequence Length Polymorphism (SSLP) in Rice (*Oryza sativa* L.) Mol Gen Genet 252:597–607 (1996).

Stephen Smith and Tim Helentjaris. DNA Fingerprinting and Plant Variety Protection. Genome Mapping in Plants.

Mathilde A. Causse, Theresa M. Fulton, Yon Gu Cho, Sang Nag Ahn, Julapark Chunwongse, Kunsheng Wu, Jinhua Xiao, Zhihong Yu, Pamela C. Ronald, Sandra E. Harrington, Gerard Second, Susan R. McCouch and Steven D. Tanksley. Saturated Molecular Map of the Rice Genome Based on an Interspecific Backcross Population. Genetics 138: 1251–1274 (Dec., 1994).

\* cited by examiner

*Primary Examiner*—Gary Benzion
*Assistant Examiner*—Melissa L. Kimball
(74) *Attorney, Agent, or Firm*—Rothwell, Figg, Ernst & Manbeck

(57) ABSTRACT

The invention relates to novel inbred rice lines designated A0044 and B0044, and the plants of inbred rice lines A0044 and B0044 as well as the rice plant and plant parts produced by the seed designated A0044. The invention also relates to methods of maintaining the male-sterile line A0044 by crossing it with the fertile line B0044 and to methods of producing hybrid rice plants by crossing inbred rice line A0044 with rice lines that act as pollen parents to restore fertility to the $F_1$ plants. Further, the invention relates to hybrid rice plants in which inbred rice line A0044 is the female parent.

12 Claims, 3 Drawing Sheets

US 6,294,717 B1

INBRED RICE LINES A0044 AND B0044

BACKGROUND OF THE INVENTION

1. Field of the Invention

The present invention relates to the breeding of rice seed and, in particular, to the identification of an inbred rice seed designated A0044 and its counterpart fertile maintainer line designated B0044. The present invention also relates to the plants produced by the cultivation of inbred rice seed designated A0044, as well as plants having A0044 as a parent. Additionally, the invention is directed to methods of maintaining the male-sterile line A0044 and of producing hybrids with inbred line A0044 as the female parent.

2. Description of Related Art

The goal of plant breeding is to combine in a single variety or hybrid various traits of agronomic or commercial interest. For field crops, these traits may include resistance to diseases and insects, tolerance to heat and drought, reduced time to crop maturity, greater yield, and improved agronomic characteristics. As a consequence of the mechanical harvesting of many crops, uniformity of plant and seed traits such as germination, stand establishment, growth rate, maturity, and fruit size are also goals of most modern plant breeding programs.

Field crops are bred through techniques that take advantage of the method of pollination of particular plant species. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at virtually all gene loci and produce uniform populations of true breeding progeny. A cross between two homozygous but genetically different lines would then produce a uniform population of hybrid plants that may be heterozygous for many gene loci. In contrast a cross of two plants each of which is heterozygous at a number of gene loci will produce a mixed population of hybrid plants that differ genetically and will not be uniform.

Rice plants (*Otyza saliva*) have perfect flowers, that is they have both male and female structures within the same flower, and rice plants are naturally self-pollinated. Breeding efforts for improvement of the rice crop have reflected this biological fact. Rice plants, left to themselves, will self-pollinate and will therefore be substantially homozygous at most gene loci.

The development of improved pure or true-breeding rice lines or varieties involves crossing two lines having different desirable characteristics by manually transferring pollen from one plant to another, and during subsequent generations, selecting plants which appear to have some combination of desirable characteristics from each parent. Pedigree breeding, which is the development of homogeneous lines during the inbreeding of populations of both self- and cross-pollinated species, is generally used in this process. Often, a third or fourth line will be included in the pedigree of a new line through crossing, as the initial two parent lines will frequently not contain all of the characters desired in a new line. During generation advance from $F_1$ to $F_2$, $F_2$ to $F_3$, $F_3$ to $F_4$, etc., homozygosity increases with each generation as the plants naturally self-pollinate, so that typically in six (6) generations, the individual plants are 98.5% homozygous.

Backcrossing is a breeding technique that can be used to improve an inbred line. Backcrossing transfers a specific desirable trait from one line or source to a line that lacks that desirable trait. This can be accomplished, for example, by first crossing a superior line S, which is a recurrent parent, to a donor line D, which is a non-recurrent parent that carries the appropriate gene(s) for the trait in question. The progeny of this cross is then mated back to the superior recurrent parent S followed by selection in the resultant progeny for the desired trait to be transferred from the non-recurrent parent D. After five or more such backcross generations with selection for the desired trait, the progeny will be homozygous for loci controlling the characteristic being transferred, but will be like the superior parent for most or almost all other genes. After this transfer of the desirable gene(s), some selfing (self-pollination) and plant selection may be required to reach homozygosity and population homogeneity. Alternatively, genetic markers can be used to select for the genotype of the recurrent parent S, and either molecular markers or plant phenotype can be used to select the desired genes from the non-recurrent parent D. With adequate markers, 2 to 3 generations of backcrossing should be adequate to return to the recurrent parent S genotype with the desired loci added from the non-recurrent parent D.

Once a single plant is homozygous at all or nearly all loci, a variety can be produced from this single plant through simple generational advance, with care being exercised to control external pollen flow and continued vigilance exercised in removing any apparent off-types in the population.

The development of Cytoplasmic Male Sterile ("CMS") hybrids in rice involves additional steps beyond the development of varieties. This hybrid system, also known as the "3-line system," is used in many crop species, including sorghum, wheat and onions. It requires, as the name implies, three (3) different lines for the complete system. These are generally called A-lines, B-lines, and R-lines. Such a three line system is described further below.

In developing hybrid rice lines, it is essential to utilize parent lines which, when combined, will give the required quality and yield characteristics that meet market standards. Secondly, both parents must have seed production performance which will result in an economically viable hybrid. Most importantly, rice hybrids must fit farmers' production systems without requiring extensive operational changes.

To accomplish the above goals, it is often essential to produce and test many hundreds of hybrids over many locations for several years to locate those rare parental combinations which meet these criteria. With several hundred important genes segregating, it is difficult to find good parent lines. Then, with, dominance, co-dominance, over-dominance, and epistasis modifying the simple interaction of the two parents, selection of parent lines for good hybrids is doubly difficult. From estimates of the number of plants involved throughout selection of R- and B-lines, and in the backcrossing of the A-line, it is likely that more than $1 \times 10^6$ genetically distinct plants will have to be examined and rejected before a single hybrid is ready for the marketplace.

SUMMARY OF THE INVENTION

The purpose and advantages of the invention will be set forth in and apparent from the description and figures that follow, as well as being learned by practice of the invention. According to the invention, there is a male-sterile rice line designated "A0044" and its fertile maintainer line designated "B0044." The invention relates to novel inbred rice lines A0044 and B0044 and the plants of inbred rice lines A0044 and B0044. The invention also relates to methods of maintaining the male-sterile line A0044 by crossing it with the fertile line B0044 and to methods of producing hybrid rice plants by crossing inbred rice line A0044 with rice lines that act as pollen parents to restore fertility to the $F_1$ plants. Further, the invention relates to hybrid rice plants in which inbred rice line A0044 is the female parent.

It is to be understood that both the foregoing general description and the following detailed description are exemplary and provided for purposes of explanation only, and are not restrictive of the invention, as claimed.

Plant Specific Definitions

Maturity—Days to 50% heading from seeding.

Maturity class—50% heading in the South:
1=Very early (less than 86 days);
2=Early (86–100 days);
3=Intermediate (101–115 days); and
4=Late (more than 115 days).

Culm angle—Stem or culm degrees from perpendicular after flowering. Rated by angle where:
1=Erect (less than 30 degrees from vertical);
3=Intermediate (about 45 degrees);
5=Open (about 60 degrees);
7=Spreading (more than 60 degrees, but the culms do not rest on the ground); and
9=Procumbent (the culm or its lower part rests on the ground surface).

Plant height—Height of the plant in centimeters, measured from soil level to top of extended panicle on main stem.

Internode color—Color of the internode after flowering scored as:
1=Green;
2=Light Gold;
3=Purple lines; and
4=Purple.

Straw strength—Measure of lodging resistance scored at maturity as:
1=Strong (no lodging);
3=Moderately strong (most plants leaning but no lodging);
5=Intermediate (most plants moderately lodged);
7=Weak (most plants nearly flat); and
9=Very weak (all plants flat)

Flag leaf size—Length of the flag leaf in centimeters and width of the flag leaf in millimeters measured after heading.

Flag leaf Pubescence—Refers to the presence or absence of pubescence on leaves. Coded as:
1=Glabrous;
2=Intermediate; and
3=Pubescent.

Flag leaf angle—Angle of flag leaf from culm measured after heading and coded as:
1=Erect;
3=Intermediate;
5=Horizontal; and
7=Descending Flag leaf blade color—Color of the leaf blade scored as:
1=Pale Green;
2=Green;
3=Dark Green;
4=Purple tips;
5=Purple margins;
6=Purple blotch; and
7=Purple.

Basal leaf sheath color—Color of the basal leaf sheath scored as:
1=Green;
2=Purple lines;
3=Light Purple; and
4=Purple.

Ligule length—Length of the ligule in millimeters, measured from base of collar to the tip at late vegetative stage.

Ligule color—Color of the ligule scored at late vegetative state and coded as:
1=White;
2=Purple lines; and
3=Purple.

Ligule shape—Shape of the ligule coded as:
1=Acute to acuminate;
2=2-Cleft; and
3=Truncate.

Collar color—Color of the ligule collar at late vegetative stage coded as:
1=Pale Green;
2=Green; and
3=Purple.

Auricle color—Color of the auricles at late vegetative stage coded as:
1=Pale Green;
2=Green; and
3=Purple.

Panicle length—Length of the panicle in centimeters, measured from the panicle base to the tip.

Panicle type—Type of panicle coded as:
1=Compact;
5=Intermediate; and
9=Open.

Secondary branching—Coded as:
1=Absent;
2=Light;
3=Heavy; and
4=Clustering.

Panicle exsertion—Percentage of panicle length exserted out of the culm after flowering.

Panicle axis—Coded as:
1=Straight; and
2=Droopy.

Shattering—Measure of percentage of shattered grains at maturity, expressed as:
1=Very low (less than 1%);
3=Low (1–5%);
5=Moderate (6–25%);
7=Moderately high (26–50%); and
9=High (more than 50%).

Panicle threshability—A measure of ease of threshability, measured as:
1=Difficult;
2=Intermediate; and
3=Easy.

Spikelet awns—Presence and morphology of awns observed after full heading and coded as:
0=Absent;

1=Short and partly awned;
5=Short and fully awned;
7=Long and partly awned; and
9=Long and fully awned.

Apiculus color—Color of the apiculus scored at maturity and expressed as:
1=White;
2=Straw;
3=Brown (tawny);
4=Red;
5=Red apex;
6=Purple; and
7=Purple apex.

Stigma color—Color of the exserted stigma expressed as.
1=White;
2=Light green;
3=Yellow;
4=Light Purple; and
5=Purple.

Stigma exsertion—A measure of the number of stigmas which remain exserted from the lemma/palea after completion of flowering. Calculated as floret with exserted stigmas as % of total florets.

Lemma and palea color—Color of lemma and palea scored at maturity and expressed as:
0=Straw;
1=Gold and/or Gold furrows on straw background;
2=Brown spots on straw (piebald);
3=Brown furrows on straw;
4=Brown (tawny);
5=Reddish to Light Purple;
6=Purple spots on straw;
7=Purple furrows on straw;
8=Purple;
9=Black; and
W=White.

Lemma and palea pubescence—Pubescence of lemma and palea expressed as:
1=Glabrous;
2=Hairs on lemma keel;
3=Hairs on upper portion;
4=Short hairs; and
5=Long hairs (velvety).

Spikelet sterility—Percentage of fertile spikelets (filled grains) measured at maturity:
1=Highly fertile (>90%);
3=Fertile (75–90%);
5=Partly sterile (50–74%);
7=Highly sterile (50% to trace); and
9=Completely sterile (0%).

Germination and seedling vigor related to low temperature—The visual assessment of germination during cool or cold temperatures. Rated as:
1=Low;
2=Medium; and
3=High.

Flowering (spikelet fertility) at low temperature—A visual rating of the effect of cold temperatures during or just prior to flowering. Rated as:
1=Low;
2=Medium; and
3=High.

Seedling vigor not related to low temperature—The visual assessment of germination when low temperatures are not an issue. Rated as:
1=Low;
2=Medium; and
3=High.

Blast—Resistance to international races of *Pyricularia oryzae*. Expressed on the following scale:
0=Immune;
1=Resistant;
3=Moderately resistant;
5=Intermediate;
7=Moderately susceptible; and
9=Susceptible.

| Group: | IB | IC | ID | IE | IG | IH |
|---|---|---|---|---|---|---|
| Number: | 1, 5, 45, 49, 54 | 1, 17 | 1, 13 | 1 | 1 | 1 |
| Resistance: | | | | | | |

Sheath blight—A measure of resistance to the vertical spread of sheath blight (*Rhizoctonia oryzae-sativae*) after inoculation or natural infection. Expressed on the following scale:
0=Immune;
1=Resistant;
3=Moderately resistant;
5=Intermediate;
7=Moderately susceptible; and
9=Susceptible.

Straighthead—This is a measure of resistance to this physiological disorder. Expressed on the following scale:
0=Immune;
1=Resistant;
3=Moderately resistant;
5=Intermediate;
7=Moderately susceptible; and
9=Susceptible.

Kernel smut—A visual rating used to measure the degree of susceptibility to *Neovossia horrida/Tilletia barclayana*. Resistance is expressed on the following scale:
0=Immune;
1=Resistant;
3=Moderately resistant;
5=Intermediate;
7=Moderately susceptible; and
9=Susceptible.

Seed Specific Definitions

Seed coat (bran) color—Color of seed coat at maturity expressed as:
1=White;
2=Light brown;
3=Speckled brown;
4=Brown;
5=Red;
6=Variable purple; and
7=Purple.

Endosperm type—Expressed as:
1=Nonglutinous (nonwaxy);
2=Glutinous (waxy); and
3=Indeterminate.
Endosperm translucency—Expressed as:
1=Clear;
5=Intermediate; and
9=Opaque.
Endosperm chalkiness—Measured as a % of total grain area (Chalky area/total area).
Scent (aroma)—Expressed as:
0=Nonscented;
1=Lightly scented; and
2=Scented.
Shape class—Length/width ratio:

|  | PADDY | BROWN | MILLED |
|---|---|---|---|
| 1 = Short | (2.2:1 and less) | (2.0:1 and less) | (1.9:1 and less) |
| 2 = Medium | (2.3:1 to 3.3:1) | (2.1:1 to 3.0:1) | (2.0:1 to 2.9:1) |
| 3 = Long | (3.4:1 and more) | (3.1:1 and more) | (3.0:1 and more) |

Grain Quality Specific Definitions

Total milling—Total milled rice as a % of rough rice.

Whole milling—Rice grains of ¾ length or more expressed as a % of rough rice.

Protein—Percent of protein in the milled grain.

Amylose—Percent of amylose in the starch of the milled grain.

Alkali spreading value—Average disintegration of 12 grains soaked in aqueous 1.7% KOH solution for 24 hours, where:

2=no effect; and
7=complete disintegration.

Amylographic paste viscosity—Starch characteristics measured on an amylograph, and Expressed in Brabender Units at: Peak, Hot Paste, Cooled Paste, 'Breakdown', and 'Setback'.

Breakdown—The peak viscosity minus the hot paste viscosity.

Cold-paste viscosity—The viscosity of a defined rice flour-water mixture at the completion of standardized, instrument-specific, heating, holding, and cooling cycle.

Consistency—Cold-paste viscosity minus hot-paste viscosity.

Hot-paste viscosity—The viscosity of a defined rice flour-water mixture after it has been heated to and held at the maximum temperature of a standardized, instrument-specific cooking cycle.

Gelatinization temperature—The temperature at which a defined flour-water mixture exhibits a measurable viscosity increase under a standardized, instrument-specific, cooking cycle (also known as "initial viscosity increase temperature").

Peak temperature, at peak viscosity—The temperature at which peak hot-paste viscosity is attained.

Peak viscosity, hot-paste—The maximum viscosity attained during heating when a standardized, instrument-specific protocol is applied to a defined rice flour-water slurry.

Setback viscosity—Cold-paste viscosity minus peak hot-paste viscosity.

BRIEF DESCRIPTION OF THE DRAWINGS

The accompanying drawings, which are incorporated in and constitute a part of this specification, illustrate the preferred embodiment of the invention, and together with the description, serve to explain the principles of the invention.

DETAILED DESCRIPTION OF THE PREFERRED EMBODIMENT

Reference will now be made in detail to the presently preferred embodiment of the seeds, plants and methods of the invention, examples of which are described herein. The present invention relates to two rice inbred lines, seeds derived from the lines, plants derived from the lines, and hybrid plants and seeds derived from the lines. Both male sterile line A0044 and the maintainer line B0044 were derived from the cross-pollination of two rice inbred lines from China, L301 and Changhui 22.

Male-sterile rice line A0044 is an indica inbred line that is best suited as a female in crosses for producing first generation $F_1$ rice hybrids. Inbred A0044 can be used to produce hybrids from approximately 100 to 140 days maturity based on the southern United States rice production region. A0044 is very suitable as a female parent for hybrid seed production as it has very high outcrossing potential and is also characterized by large panicles. Inbred A0044 in most hybrid combinations has excellent yield, and standard US rice quality.

The invention is also directed to methods for producing a rice plant by crossing a first parent rice plant with a second parent rice plant wherein the first parent rice plant is an inbred rice plant from the A0044 line. Thus, any such methods using the inbred rice line, A0044, are part of this invention, including backcrosses, hybrid production, crosses to populations, and the like. All plants produced using inbred rice line A0044 as a parent are within the scope of this invention. Advantageously, the inbred rice line is used in crosses with other, different, rice inbreds to produce first generation ($F_1$) rice hybrid seeds and plants with superior characteristics. Also, the male-sterile inbred rice line A044 is maintained by pollination by male-fertile line B0044, and this method of maintaining rice line A0044 is within the scope of this invention.

As used herein, the terms "plant and plant parts" include plant cells, plant protoplasts, plant cell tissue culture from which rice plants can be regenerated, plant calli, plant clumps, and plant cells that are intact in plants or parts of plants, such as embryos, pollen, flowers, roots, root tips and the like.

Figure 1:
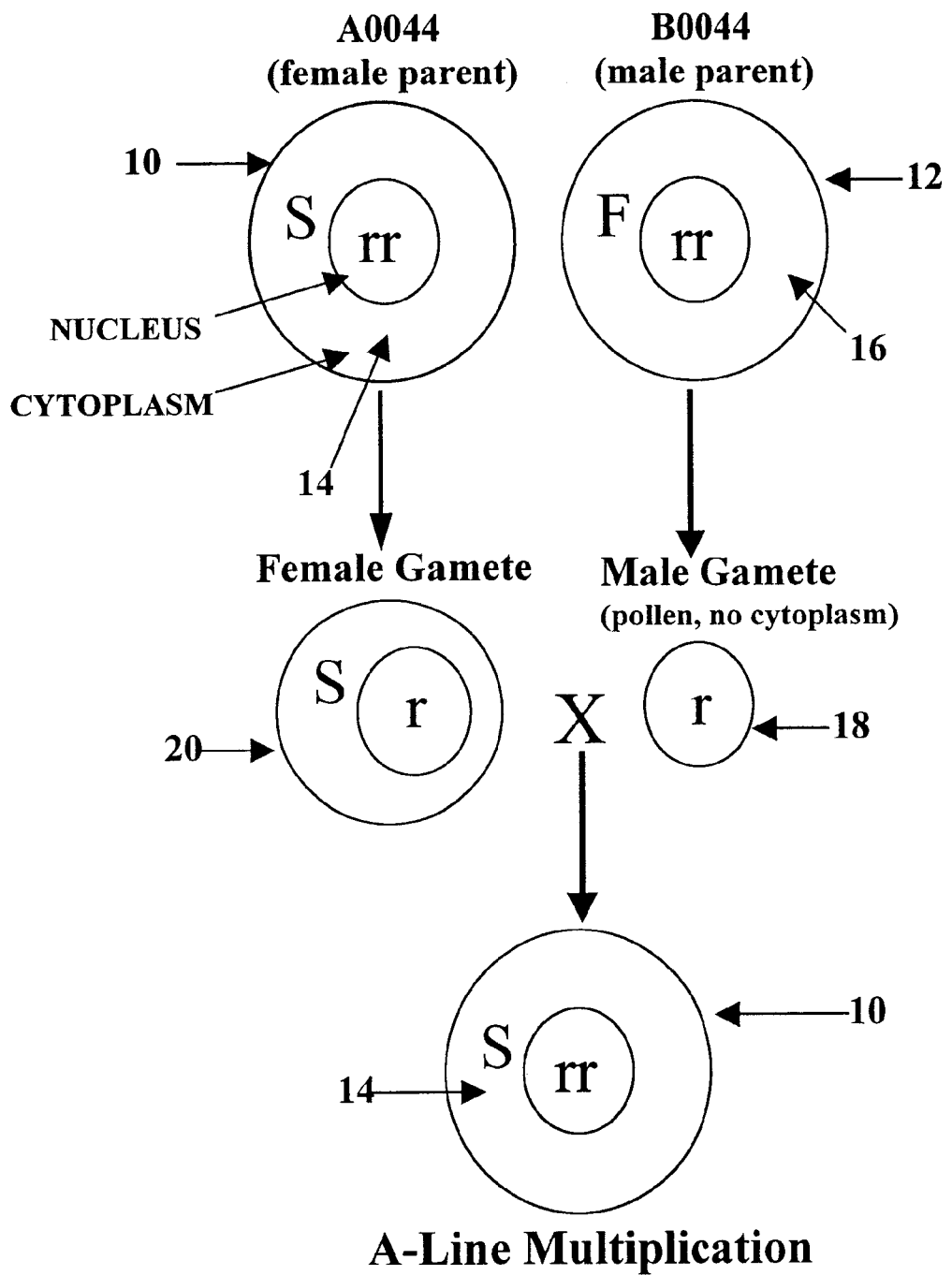
FIG. 1 illustrates the genetic mechanism of A-line multiplication according to the present invention.

Referring now to FIG. 1, a system for maintenance of the A-line by crossing the A-line 10 with B-line 12 is shown.

In FIG. 1, S refers to sterile cytoplasm 14; F refers to normal (fertile) cytoplasm 16; R denotes a dominant nuclear gene which restores fertility and r denotes a recessive allele which does not restore fertility. The A-line is male-sterile due to its cytoplasm 14, and therefore cannot produce viable pollen, so A-line seed must be maintained and increased through pollination of the A-line by the B-line, also called a maintainer line. This maintenance is accomplished when the pollen 18 of the B-line fertilizes the female gamete 20 of the A-line to produce additional A-line seeds. Each backcross, or A-line increase (which is a bulk backcross), will bring the nuclear genetic constitution of the A-line closer to that of the B-line. However, the sterile determinants in the cytoplasm of the A-line will not be converted to the fertile type because B-line pollen 18 carries only the nuclear genome without restorer genes and not the fertility trait determined by B-line cytoplasm 16. In early generations, the increase of A-line seed may be through hand pollination, but as seed volumes increase, this process must be conducted on increasingly large field scale.

Figure 2:
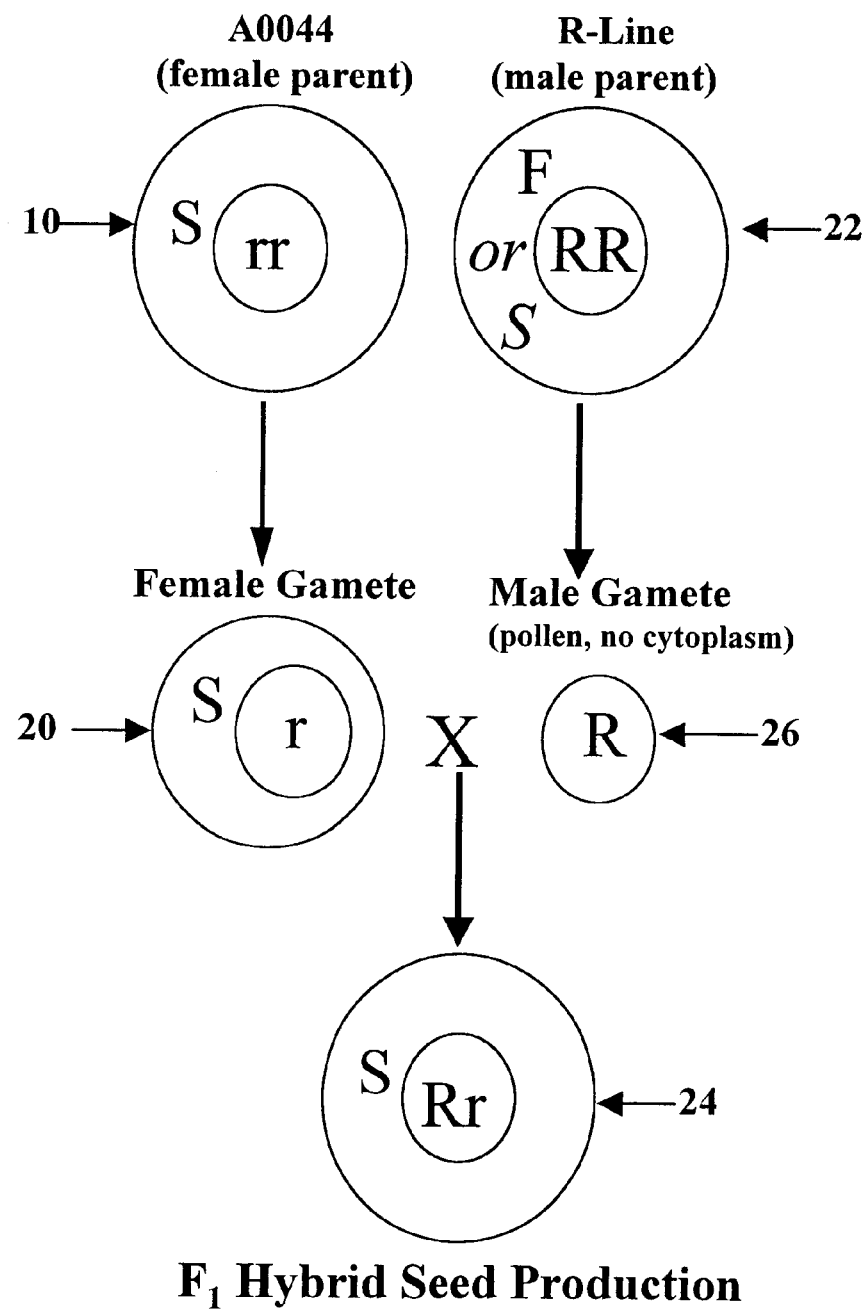
FIG. 2 illustrates the genetic mechanism hybrid seed production according to the present invention.

Referring now to FIG. 2, the process required for production of hybrid seed by crossing the A-line and an R-line, which involves the field level crossing of an A-line plant 10 with an R-line plant 22 for the production of $F_1$ hybrid seed 24 is shown.

In FIG. 2, hybrid plant 24 is produced by crossing the A-line with a restorer line ("R-line"), which has dominant nuclear genetic loci for restoration. The $F_1$ hybrid will have the sterile cytoplasm of the A-line, but the restorer genes from the R-line will result in a fertile $F_1$ hybrid. This production of the hybrid is accomplished when the pollen 26 of the R-line fertilizes the female gamete 20 of the A-line to produce $F_1$ hybrid seeds 24. Like all CMS hybrids, the $F_2$ of this hybrid will segregate for sterility and all genetic factors which differ between the parents.

Figure 3:
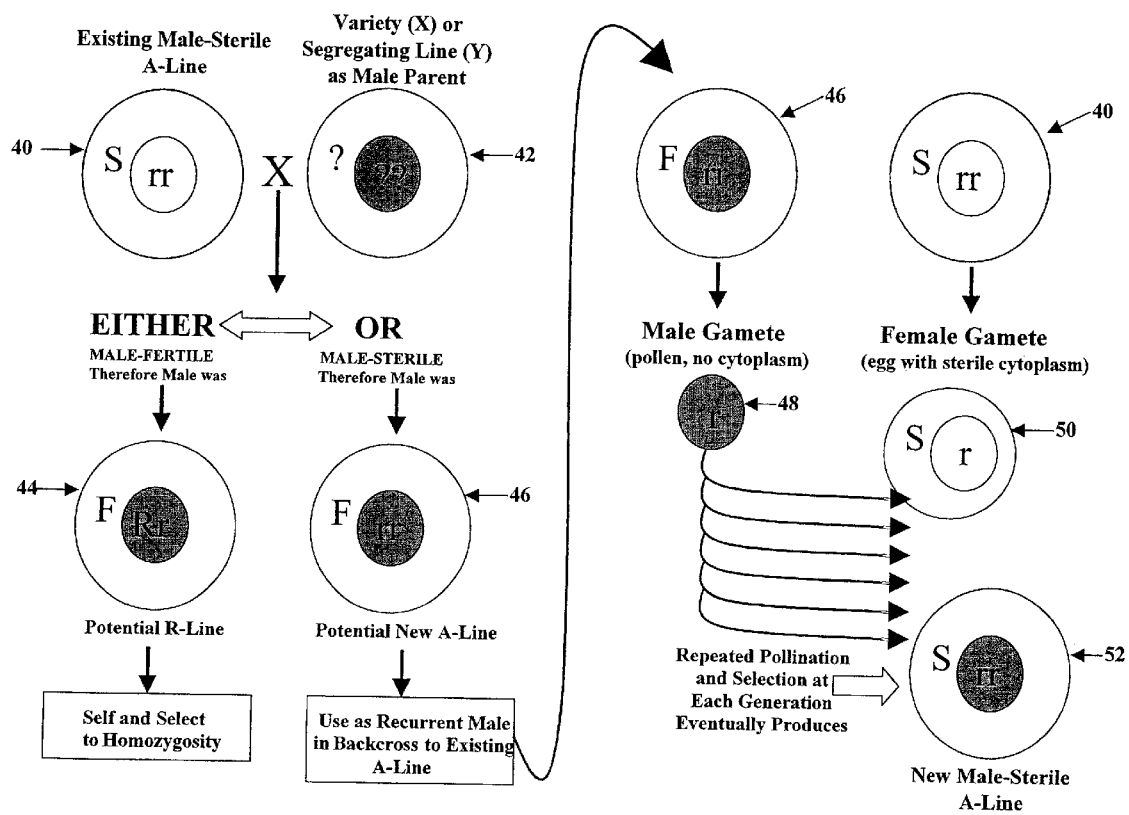
FIG. 3 illustrates the development of new A-lines from their maintainer B-lines according to the present invention.

Referring now to FIG. 3, in the development of new A-line/B-line pairs, a variety X developed in the normal varietal program, or a segregating line Y from a pedigree program, is selected and test-crossed with an existing male-sterile A-line as shown. The existing A-line 40 is crossed with a plant 42 of variety X or segregating line Y. If the $F_1$ progeny of this cross is fertile 44, then the variety (X or Y) is an R-line. Fertile seed from this line 44 will by multiplied through selfing and plant selection known in the art to achieve homozygosity to create a stable R-line. About 70% of the time the result will be a partially fertile plant, and will not useful for B-lines or R-lines directly.

If the $F_1$ progeny plants are sterile, however, then the variety (X or Y) is a B-line 46. If this B-line has the appropriate genetic characteristics, such as exserted stigmas, proper leaf type, short plant height, etc., a series of paired plant-to-plant backcrosses, typically 5–7 backcrosses are performed crossing the male gamete 48 of the B-line 46 with the female gamete 50 of the existing A-line 40. These backcrosses are used to convert the genome of the existing A-line into a new A-line 52 with the nuclear genetics of the (X or Y) B-line, while maintaining the sterile cytoplasm of the original A-line 40. This process leads to an A/B pair, genetically isogenic at the nuclear level, but containing different cytoplasms, one fertile 46 and one sterile 52.

Initially, many hybrid combinations with each new A-line or each new R-line will be produced by hand pollination or other small scale techniques, and the $F_1$ progeny will be tested at small scale. As more information is obtained, the scales of seed production and testing are both increased, until ultimately, both seed production and $F_1$ hybrid grain production will be done at commercial farm scale.

B0044, the male-fertile maintainer line for A0044, was derived from a cross-pollination of two rice-inbred lines L301 and Changhui 22, both developed in China. The origin and breeding history of A0044 and B0044 occurred as follows.

Rice seeds acquired in a germplasm purchase from Ring Around Products, Inc. and a part of their A-line breeding program were planted at the RiceTec, Inc. research farm in Alvin, Tex. Plants in the plot #8571 and the plot #8572, whose pedigrees were 9010-4-1 and 9010-3-1/9010-4-1 respectively, were observed to be desirable male-fertile maintainer line and male-sterile lines. As used herein, the plot numbers and pedigrees are internal designations of RiceTec. The second plant in the plot #8571 was selected and crossed with a selected sterile plant on plot #8572. The seeds from the second plant of plot #8571 and crossed seeds on plot #8572 were harvested respectively.

The harvested seeds from the second plant of plot #8571 and crossed seeds from plot #8572 were planted in a greenhouse in Alvin, Tex. as the plot numbers 2643 and 2644 with the pedigrees as (RA9010-4-1)-2 and (BC)1.RA9010-3-1/(RA9010-4-1)-2, respectively. The plants in the plot #2643 were selected and backcrossed with selected sterile plants on plot #2644. The seeds from selected plants from plot # 2643 and backcrossed seeds from plot #2644 were bulk harvested respectively. The pedigrees for them were (RA9010-4-1)-2-2643 and (BC)2.RA9010-3-1/(RA9010-4-1)-2-2643.

The bulk harvested seeds from selected plants of plot #2643 and plot #2644 were planted in Alvin, Tex. with the plot numbers 4273 and 4274, respectively. Plants in plot #4273 were selected again and backcrossed with selected sterile plants on plot #4274. The seeds from selected plants on plot #4273 and crossed seeds from plot #4274 were bulk harvested respectively.

The seeds harvested from plot #4273 and plot #4274 were planted in Alvin, Tex. in a micro-increase experiment with designated plot numbers 95M3 and 95M4, respectively. The seeds from plot #95M3 were bulk harvested and assigned RiceTec, Inc. permanent identification number B0044 and the seeds from plot #95M4 were bulk harvested and assigned RiceTec, Inc. permanent identification number A0044.

Plants and seeds of male-sterile inbred A0044 are characterized by the properties shown in Table 1 (see above for the definitions related to the terms used in Table 1).

TABLE 1

VARIETY DESCRIPTION INFORMATION
INBRED = A0044

Type: Indica                       Region Best Adapted: Most Regions

A. Maturity: 60–65 days from planting to 50% heading
    Maturity Group: Very early (less than 86 days)
B. Culm:
    Angle (degrees from perpendicular after flowering): Erect
    (less than 30 degrees)
    Plant Height: 80 cm
    Height Class: Semidwarf
    Internode Color (after flowering): Green
    Strength (lodging resistance): Moderately strong
    (most plants leaning)
C. Flag Leaf (after flowering)
    Length: 30 cm
    Width: 2.0 cm
    Pubescence: Pubescent
    Leaf Angle (after flowering): Intermediate
    Blade Color: Green
    Basal Leaf Sheath Color: Green
D. Ligule
    Color (late vegetative state): White
    Shape: 2-cleft
    Collar Color: Pale Green
    Auricle Color (late vegetative state): Pale Green

TABLE 1-continued

VARIETY DESCRIPTION INFORMATION
INBRED = A0044

Type: Indica                  Region Best Adapted: Most Regions

E. Panicle
    Length: 24 cm
    Type: Intermediate
    Secondary Branching: Heavy
    Exsertion (near maturity): 75% exserted
    Axis: Droopy
    Shattering: Moderate (6–25%)
    Threshability: Easy
F. Grain (Spikelet)
    Awns (after full heading): Absent
    Apiculus Color (at maturity): White
    Stigma Color: White
    Stigma exsertion (at flowering): Very high (>60%)
    Lemma and palea color (at maturity): Straw
    Lemma and palea pubescence: Short hairs
    Spikelet sterility (at maturity): Complete sterile (100%)
G. Grain (seed)
    Seed coat (bran) color: White
    Endosperm type: Non-glutinous (non-waxy)
    Endosperm translucency: Clear
    Endosperm chalkiness: Medium (10–20% of sample)
    Scent (aroma): Nonscented
    Shape class: Long
    Measurements (milled rice): Length = 6.8 mm,
    Width = 2.2 mm, L/W = 3.1
    1000-grain weight: 24 grams
    Milling quality: 67.9% hulls
    Milling yield (% whole kernel (head) rice to rough rice): 59.7%
    Amylose: 26.1%
    Alkali spreading value (1.5% KOH solution): 6.0
    Gelatinization temperature type: Intermediate
H. Resistance to Low Temperature
    Germination and seeding vigor: Medium
    Flowering (spikelet fertility): Medium
I. Seeding Vigor Not Related to Low Temperature: Medium
J. Blast Resistance (*Pyricularia oryzae*)
Type: Resistant

| Group: | IB | IC | ID | IE | IG | IH |
|---|---|---|---|---|---|---|
| Number: | 1, 5, 45, 49, 54 | 1, 17 | 1, 13 | 1 | 1 | 1 |
| Resistance: | 2, 2, 2 | 2 | 2 | 2 | 2 | 2 |

K. Resistance to Other Diseases:
    Sheath Blight (*Rhizoctonia oryzae-sativae*):
    7 (check = Gulfmont = 7)
    Straight head: 7, (check: Cypress = 2, Gulfmont = 2)
    Kernel Smut (*Neovossia horrida*) (*Tilletia barclayana*):
    4, (check = Cypress = 7)

The inbred designated A0044 has shown uniformity and stability within the limits of environmental influence for all the traits as described in Table 1 above. Most of the data in the Variety Description Information were collected at the Alvin, Texas research farm. The inbred has been backcrossed a sufficient number of generations with careful attention paid to uniformity of plant type to ensure homozygosity and phenotypic stability. The line has been increased both by hand and in isolated fields with continued observation for uniformity. No variant traits have been observed or are expected in A0044

Inbred rice line A0044, being substantially homozygous, can be reproduced by planting seeds of B0044 in the same field side-by-side with adequate isolation or hand-crossed with B0044 pollen and harvested from the A0044 plants, using techniques known in the art.

The following text and tables present data on the yield performance of the inbred A0044/B0044 as compared to another RiceTec A/B pair (A0024/B0024) and the physical characterization of floral parts as compared to a common Chinese line (V20A). Also presented are data on the field yield performance of the hybrid produced by crossing A0044 with R612, and of five other hybrids with A0044 as the female parent, as compared to Cypress, a common US variety.

In the examples that follow, A0044 and B0044 are compared to other CMS sterile lines from China and from the breeding program at RiceTec. The line from China chosen for comparison is V20A, a CMS line developed in the 1970s in China, and still widely used today in hybrid seed production there. The RiceTec line used is A0024, one of the first CMS lines selected for use in RiceTec in 1991.

Comparisons of yield for the A-lines are shown in Table 4a. These data are collected under high pollen load situations, so that this test is a measure of seed yield potential in a hybrid production system. A0044 shows significantly higher yield in each year, and, on average, higher yield than the earlier developed A-line A0024. Table 4b shows the comparison of B0044 and B0024 in 3 years of yield testing. B0044 shows higher average yield.

TABLE 4a

Comparison of Yield for Inbred A-Lines A0044 and A0024

| | 1996 | 1997 | 1998 | Average |
|---|---|---|---|---|
| A0044 | 1996 | 2049 | 2943 | 2329 |
| A0024 | 1319 | 1179 | 1251 | 1249 |
| Locations | 1 | 1 | 1 | 3 (total) |
| Probability | 0.0022 | 0.0009 | 0.0000 | 0.0002 |

Yields in Pounds per Acre

TABLE 4b

Comparison of Yield for Inbred B-Lines B0044 and B0024

| | 1996 | 1997 | 1998 | Average |
|---|---|---|---|---|
| B0044 | 6187 | 6470 | 6794 | 6483 |
| B0024 | 7095 | 5194 | 5637 | 5972 |
| Locations | 2 | 2 | 2 | 6 (total) |
| Probability | 0.0015 | 0.0003 | 0.0032 | 0.0002 |

Yields in Pounds per Acre

Table 4c shows a comparison of the effective outcrossing, which combines the yield potential of the B-line as a measure of possible yield, and the A-line yield as the actual yield. The results show that A0044 has effective outcrossing 72% greater than A0024 in small field situations.

TABLE 4c

Comparison of Effective Seed Set of A0044 and A0024 as a Percentage of their B-Line

| | 1996 | 1997 | 1998 | Average |
|---|---|---|---|---|
| A0044 | 32.3% | 31.7% | 43.3% | 35.9% |
| A0024 | 18.6% | 22.7% | 22.2% | 20.9% |
| Locations | 1 | 1 | 1 | 3 (total) |

Percentage Calculated as Yield of A-Line/Yield of B-Line

Tables 5a–5c show comparisons of A0044 with V20A, a common CMS sterile line in China. Table 5a compares the number of florets which have either one or both stigma exserted at flowering. A0044 has more than twice as many florets with at least one stigma exserted, and more than five (5) times as many florets with both stigmas exserted per panicle. Because florets per panicle are different, the percentage comparisons are included. On a percentage basis, A0044 has about 70% more florets with at least one stigma exserted, and about four (4) times as many with both stigmas exserted.

TABLE 5a

Comparison of A0044 and V20A for Stigma Exsertion

|  | (1+) Stigmas | 2 Stigmas | Total Florets |
|---|---|---|---|
|  | Florets with Exserted Stigmas | | |
| V20A | 41.67 | 12.67 | 190.67 |
| A0044 | 88.33 | 69.00 | 253.33 |
|  | (1+) Stigmas | 2 Stigmas | % Stigma |
|  | Percent of Florets with Exserted Stigmas | | |
| V20A | 21.72 | 6.52 | 28.24 |
| A0044 | 34.93 | 27.09 | 62.02 |

Table 5b compares the degree of opening of the lemma and palea of A0044 and V20A. This is a measure of the separation of the tip of the lemma and palea at peak flowering time. A0044 has slightly narrower aperture than V20A.

TABLE 5b

Comparison of A0044 and V20A for Opening of Lemma and Palea

|  | 0 Stigma | 1 Stigmas | 2 Stigmas |
|---|---|---|---|
| V20A | 2.00 | 3.65 |  |
| A0044 | 2.87 | 3.23 | 4.13 |

Table 5c compares physical differences of A0044 and V20A. A0044 has white stigmas and auricles, and longer flag leaves compared to V20A which has purple stigmas and auricles, and shorter flag leaves.

TABLE 5c

Comparison of Physical Characteristics of A0044 and V20A

|  | Stigma | Auricle | Sheath Color | Flag Leaf Length (mm) |
|---|---|---|---|---|
| V20A | Black, thin on end | Green with purple edge | Purple | 29.42 |
| A0044 | White, bushy | White to light yellow | Green | 48.18 |

These results show that A0044 has a better floral structure for outcrossing than does the leading Chinese sterile line V20A, and significantly better field seed yields than the RiceTec A-line A0024.

In the examples that follow, the traits and characteristics of rice hybrid plants and grain resulting from a cross of A0044 and a pollinator line are compared with Cypress, a commonly grown rice variety in the United States. The data were collected in multi-location, replicated trials.

The results in Table 6a compare yield, plant height and milling yields of Cypress and the hybrid line produced by crossing A0044 with R612. The hybrid has substantially and significantly higher yield than Cypress, is significantly taller than Cypress, and has significantly lower total and whole milling yields.

TABLE 6a

Comparison of Field Characteristics of Hybrid Produced from A0044 by R612 and Cypress

|  | Yield | Plant Ht (cm) | Total % | Whole % |
|---|---|---|---|---|
| Cypress | 6302 | 93 | 69.2 | 61.5 |
| A0044 by R612 | 7572 | 118 | 66.3 | 52.5 |
| Locations | 29 | 9 | 10 | 10 |
| Difference | 1270.41 | 24.77 | 2.94 | 9.06 |
| Probability | .000*** | .000*** | .032** | .004*** |

Yields in Pounds per Acre
Significance levels are indicated as: *=10% =5% *=1%

Table 6b compares grain quality data for Cypress and the hybrid line produced by crossing A0044 with R612. The hybrid grain has significantly higher amylose, alkaline spreading value ("ASV") and starch index ("SI") than Cypress. The hybrid grain is significantly longer and wider than Cypress. The hybrid line produced by crossing A0044 with R612 also has a significantly higher grain chalk rating than Cypress.

TABLE 6b

Comparison of Grain Quality Data of a Hybrid Produced from A0044 by R612 and Cypress

|  | Amylose | ASV | SI | Length | Width | L/W | Chalk |
|---|---|---|---|---|---|---|---|
| Cypress | 23.98 | 5.41 | 28.95 | 6.66 | 2.06 | 3.23 | 4.82 |
| A0044 by R612 | 24.75 | 5.81 | 30.17 | 6.78 | 2.21 | 3.07 | 12.87 |
| Locations | 10 | 6 | 10 | 16 | 16 | 16 | 16 |
| Difference | −0.77 | −0.40 | −1.22 | −0.12 | −0.15 | 0.16 | −8.05 |
| Probability | 0.054 | .001*** | .006*** | .015** | .000*** | .000*** | .017** |

Significance levels are indicated as: * = 10%   = 5%  * = 1%

Table 6c compares starch quality parameters for Cypress and the hybrid line produced by crossing A0044 with R612 as measured by amylographic analysis. The hybrid line produced by crossing A0044 with R612 has a higher peak and longer peak time than Cypress, identical trough time and paste temperatures, and lower breakdown and setback values.

TABLE 6c

Comparison of Starch Quality Parameters of a Hybrid Produced from A0044 by R612 and Cypress

| | Peak | Peak Time | Trough | Trough Time | Paste Temp | Paste Time | Final Visc | Break-down | Setback | Consistency |
|---|---|---|---|---|---|---|---|---|---|---|
| Cypress | 345.86 | 8.96 | 118.32 | 13.20 | 72.81 | 4.86 | 234.92 | 227.57 | −111.04 | 116.65 |
| A0044 by R612 | 375.28 | 9.23 | 152.69 | 13.19 | 72.45 | 4.74 | 297.24 | 222.63 | −78.00 | 144.75 |
| Locations | 3 | 3 | 3 | 3 | 3 | 3 | 3 | 3 | 3 | 3 |
| Difference | −29.41 | −.027 | −34.37 | 0.01 | 0.36 | 0.13 | −62.32 | 4.94 | −33.04 | −28.10 |
| Probability | 0.055 | .002*** | .005*** | 0.849 | 0.412 | 0.259 | .000*** | 0.423 | .019** | .004 |

Significance levels are indicated as: * = 10%   = 5%  * = 1%

Table 7 shows comparative data for yield of 5 other hybrids, each of which has A0044 as the female parent. In each case the hybrids have a higher yield than Cypress, but in only 3 of the 5 hybrids is the difference significant. The hybrid produced by crossing A0044 with R101 and the hybrid produced by crossing A0044 with R115 show highly significant yield advantages over the common variety Cypress.

TABLE 7

Yield Advantage of Hybrids with A0044 as a parent over Cypress

| Hybrid | Cypress Yield | Hybrid Yield | Diff | Prob | n |
|---|---|---|---|---|---|
| A0044 by R612 | 6302 | 7572 | 1270 | 0 | 29 |
| A0044 by R034 | 6609 | 6862 | 253 | .743 | 4 |
| A0044 by R101 | 6133 | 7693 | 1560 | .049** | 8 |
| A0044 by R115 | 6618 | 7873 | 1255 | .007*** | 14 |
| A0044 by R120 | 6708 | 7894 | 1186 | .027** | 11 |
| A0044 by R134 | 6821 | 7454 | 633 | .246 | 9 |

Yields in Pounds per Acre
Significance levels are indicated as: * = 10%   = 5%  * = 1%

Applicants have made available to the public without restriction a deposit of at least 2500 seeds of Inbred Rice Lines A0044 and B0044 with the American Type Culture Collection ("ATCC"), Rockville, Md. 20852 USA. These deposits were made on Oct. 11, 1999, and the deposit of Inbred Rice Line A0044 has been assigned ATCC Deposit No. PTA-837 and the deposit of Inbred Rice Line B0044 has been assigned ATCC Deposit No. PTA-836. These deposits of Inbred Rice Line A0044 and Inbred Rice Line B0044 will be maintained in the ATCC depository for a period of 30 years, or 5 years after the most recent request, or for the effective life of the patent, whichever is longer, and Applicants will replace it if it becomes nonviable during that period.

Although reference has been made to particular hybrids of inbred rice line A0044 of the present invention, those hybrids are discussed for the purpose of explanation and it is understood that other hybrids having A0044 as a parent are encompassed by the invention. It also will be apparent to those skilled in the art that various modifications and variations can be made in the performance of the methods, without departing from the scope or spirit of the invention.

Other embodiments of the invention will be apparent to those skilled in the art from consideration of the specification and practice of the invention disclosed herein.

It is intended that the specification and examples be considered as exemplary only, with the true scope and spirit of the invention being indicated by the following claims.

What is claimed is:

1. Inbred Rice Seed designated A0044 and having ATCC Accession No. PTA-837.

2. A rice plant or its plant parts produced by the seed of claim 1.

3. An inbred rice plant having a genotype capable of expressing all the physiological and morphological characteristics of A0044, a representative sample of which has been deposited with American Type Culture Collection and having Accession No. PTA-837.

4. A rice plant regenerated from the cells or protoplasts of a culture of tissue selected from the group consisting of meristemetic tissue, immature embryos, microspores and pollen taken from a plant according to claim 2 and having a genotype capable of expressing all the physiological and morphological characteristics of inbred rice plant A0044.

5. Inbred Rice Seed designated B0044 and having ATCC Accession No. PTA-836.

6. A rice plant or its plant parts produced by the seed of claim 5.

7. An inbred rice plant having a genotype capable of expressing all the physiological and morphological characteristics of B0044, a representative sample of which has been deposited with American Type Culture Collection and having Accession No. PTA-836.

8. A rice plant regenerated from the cells or protoplasts of a culture of tissue selected from the group consisting of meristemetic tissue, immature embryos, microspores and pollen taken from a plant according to claim 6 and having a genotype capable of expressing all the physiological and morphological characteristics of inbred rice plant B0044.

9. A method of maintaining the seed of male-sterile inbred rice line A0044, a representative sample of which has been deposited with American Type Culture Collection and having Accession No. PTA-837, comprising the steps of:

(a) planting in pollinating proximity seeds of rice inbred lines A0044 and rice inbred line B0044, a representative sample of which has been deposited with American Type Culture Collection and having Accession No. PTA-836;

(b) cultivating rice plants resulting from the planting until the time the plants bear flowers;

(c) allowing pollination of inbred line A0044 by inbred line B0044;

(d) harvesting seeds produced on male-sterile plants of the inbred line A0044.

10. A method of producing hybrid rice having the characteristics of high yield comprising the steps of:
(a) planting in pollinating proximity seeds of rice inbred line A0044, a representative sample of which has been deposited with American Type Culture Collection and having Accession No. PTA-837, and another inbred line;
(b) cultivating rice plants resulting from the planting until the time the plants bear flowers;
(c) allowing pollination of inbred line A0044 by the other inbred line;
(d) harvesting seeds produced on male-sterile plants of the inbred line A0044.

11. $F_1$ hybrid rice seed and plants therefrom produced by crossing the inbred rice plant of claim 3 with another rice plant.

12. A rice plant capable of expressing all the physiological and morphological characteristics of rice plants grown from rice seed designated A0044, a representative sample of which has been deposited with American Type Culture Collection and having Accession No. PTA-837.

* * * * *